(12) United States Patent
King

(10) Patent No.: US 7,493,898 B2
(45) Date of Patent: Feb. 24, 2009

(54) INHALATION APPARATUS

(75) Inventor: Russell King, Baldwin Park, CA (US)

(73) Assignee: Healthline Medical, Inc., Baldwin Park, CA (US)

( * ) Notice: Subject to any disclaimer, the term of this patent is extended or adjusted under 35 U.S.C. 154(b) by 708 days.

(21) Appl. No.: 11/105,093

(22) Filed: Apr. 13, 2005

(65) Prior Publication Data

US 2006/0231090 A1 Oct. 19, 2006

(51) Int. Cl.
*B05B 1/26* (2006.01)
*A61M 11/00* (2006.01)

(52) U.S. Cl. .......................... 128/200.18; 128/200.14; 128/200.21; 128/200.24; 239/338; 137/39

(58) Field of Classification Search ............ 128/200.14, 128/200.18, 200.24, 203.15, 205.24, 897, 128/203.28, 203.12, 200.21, 207.12, 911, 128/207.14, 205.13, 204.18, 204.25; 138/39, 138/42; 137/527.8, 493.5, 493

See application file for complete search history.

(56) References Cited

U.S. PATENT DOCUMENTS

| | | | | |
|---|---|---|---|---|
| 1,156,432 A * | 10/1915 | Peavey | ....................... | 184/55.1 |
| 2,056,022 A * | 9/1936 | Steenstrup | ................... | 138/42 |
| 2,450,610 A * | 10/1948 | Pierce | ................... | 128/205.27 |
| 3,358,749 A * | 12/1967 | Chisholm et al. | ........... | 165/141 |
| 3,381,713 A * | 5/1968 | Jacobsen | ..................... | 138/39 |
| 3,636,983 A * | 1/1972 | Keyser | ........................ | 138/39 |
| 3,664,337 A * | 5/1972 | Lindsey et al. | ......... | 128/200.18 |
| 3,874,379 A * | 4/1975 | Enfield et al. | .......... | 128/200.18 |
| 3,903,884 A * | 9/1975 | Huston et al. | .......... | 128/200.18 |
| 3,945,378 A * | 3/1976 | Paluch | ................... | 128/201.13 |
| 4,040,256 A * | 8/1977 | Bosche et al. | ............... | 405/119 |
| 4,198,969 A * | 4/1980 | Virag | .................... | 128/200.21 |
| 4,200,093 A * | 4/1980 | Camp | .................... | 128/200.14 |
| 4,225,542 A * | 9/1980 | Wall et al. | ................... | 261/142 |
| 4,231,973 A * | 11/1980 | Young et al. | ............... | 261/78.2 |
| 4,331,140 A * | 5/1982 | Hallsey | ................. | 128/204.26 |
| 4,521,038 A * | 6/1985 | Cerny | .......................... | 285/24 |
| 4,560,519 A * | 12/1985 | Cerny | ......................... | 261/78.2 |
| 4,598,704 A * | 7/1986 | Bordoni et al. | ........ | 128/200.14 |
| 4,676,239 A * | 6/1987 | Humphrey | ............ | 128/205.17 |
| 4,782,828 A * | 11/1988 | Burnett et al. | ......... | 128/200.14 |
| 4,792,421 A * | 12/1988 | Stori | ....................... | 261/122.1 |
| 4,823,784 A * | 4/1989 | Bordoni et al. | ........ | 128/200.14 |
| 4,824,614 A * | 4/1989 | Jones | .......................... | 261/76 |
| 4,856,510 A * | 8/1989 | Kowalewski | ........... | 128/207.15 |
| 4,907,581 A * | 3/1990 | King | ..................... | 128/200.18 |
| 4,919,170 A * | 4/1990 | Kallinich et al. | ............. | 138/39 |
| 5,020,530 A * | 6/1991 | Miller | ................... | 128/203.28 |
| 5,042,467 A * | 8/1991 | Foley | .................... | 128/200.23 |
| 5,054,478 A * | 10/1991 | Grychowski et al. | ... | 128/200.21 |
| 5,067,487 A * | 11/1991 | Bauman | ................ | 128/205.13 |
| 5,086,765 A * | 2/1992 | Levine | .................. | 128/200.21 |
| 5,092,366 A * | 3/1992 | Sakamoto | ..................... | 138/37 |
| 5,099,833 A * | 3/1992 | Michaels | ............... | 128/200.14 |
| 5,116,257 A * | 5/1992 | Szlaga | .......................... | 137/43 |
| 5,309,906 A * | 5/1994 | LaBombard | ........... | 128/207.14 |

(Continued)

*Primary Examiner*—Justine R Yu
*Assistant Examiner*—Clinton Ostrup

(57) ABSTRACT

An inhalation apparatus for medicinal use which will deliver aerosolized medication to the patient that comprises up to about 80% of the medication aerosolized in essentially the same particle size distribution of the aerosol mist that originates from the nebulizer which produces the mist. The apparatus also provides delivered dose consistency over a wide range of patient breathing parameters.

18 Claims, 11 Drawing Sheets

U.S. PATENT DOCUMENTS

| | | | | |
|---|---|---|---|---|
| 5,415,161 A | * | 5/1995 | Ryder | 128/200.23 |
| 5,497,765 A | * | 3/1996 | Praud et al. | 128/200.23 |
| 5,598,836 A | * | 2/1997 | Larson et al. | 128/200.23 |
| 5,687,912 A | * | 11/1997 | Denyer | 239/343 |
| 5,720,282 A | * | 2/1998 | Wright | 128/207.14 |
| 5,727,542 A | | 3/1998 | King | |
| 5,738,087 A | * | 4/1998 | King | 128/200.23 |
| 5,752,502 A | | 5/1998 | King | |
| 5,800,059 A | * | 9/1998 | Cooke et al. | 366/337 |
| 5,826,575 A | * | 10/1998 | Lall | 128/205.12 |
| 5,865,171 A | * | 2/1999 | Cinquin | 128/203.12 |
| 5,865,172 A | * | 2/1999 | Butler et al. | 128/203.12 |
| 5,916,640 A | * | 6/1999 | Liu et al. | 427/475 |
| 5,983,893 A | * | 11/1999 | Wetterlin | 128/203.15 |
| 5,988,162 A | * | 11/1999 | Retallick, III | 128/203.12 |
| 6,014,972 A | * | 1/2000 | Sladek | 128/203.12 |
| 6,073,628 A | * | 6/2000 | Butler et al. | 128/203.12 |
| 6,244,576 B1 | * | 6/2001 | Tsai | 261/141 |
| 6,250,301 B1 | * | 6/2001 | Pate | 128/203.26 |
| 6,390,090 B1 | * | 5/2002 | Piper | 128/203.28 |
| 6,439,231 B1 | * | 8/2002 | Fukunaga et al. | 128/207.14 |
| 6,494,202 B2 | * | 12/2002 | Farmer | 128/200.23 |
| 6,513,519 B2 | * | 2/2003 | Gallem | 128/200.14 |
| 6,539,939 B2 | * | 4/2003 | Rubin | 128/203.15 |
| 6,595,203 B1 | * | 7/2003 | Bird | 128/200.21 |
| 6,681,767 B1 | * | 1/2004 | Patton et al. | 128/203.15 |
| 6,904,908 B2 | * | 6/2005 | Bruce et al. | 128/200.23 |
| 7,204,245 B2 | * | 4/2007 | Johnson et al. | 128/200.14 |
| 7,207,329 B2 | * | 4/2007 | Bowden | 128/203.12 |
| 7,225,805 B2 | * | 6/2007 | Bacon | 128/200.23 |
| 7,275,539 B2 | * | 10/2007 | Gippert | 128/204.12 |
| 2002/0162554 A1 | * | 11/2002 | Loescher | 128/205.24 |
| 2004/0089296 A1 | * | 5/2004 | Bowden | 128/203.12 |
| 2004/0231665 A1 | * | 11/2004 | Lieberman et al. | 128/200.14 |
| 2005/0165304 A1 | * | 7/2005 | Albertelli | 600/431 |
| 2005/0217667 A1 | * | 10/2005 | Dhuper et al. | 128/200.23 |

* cited by examiner

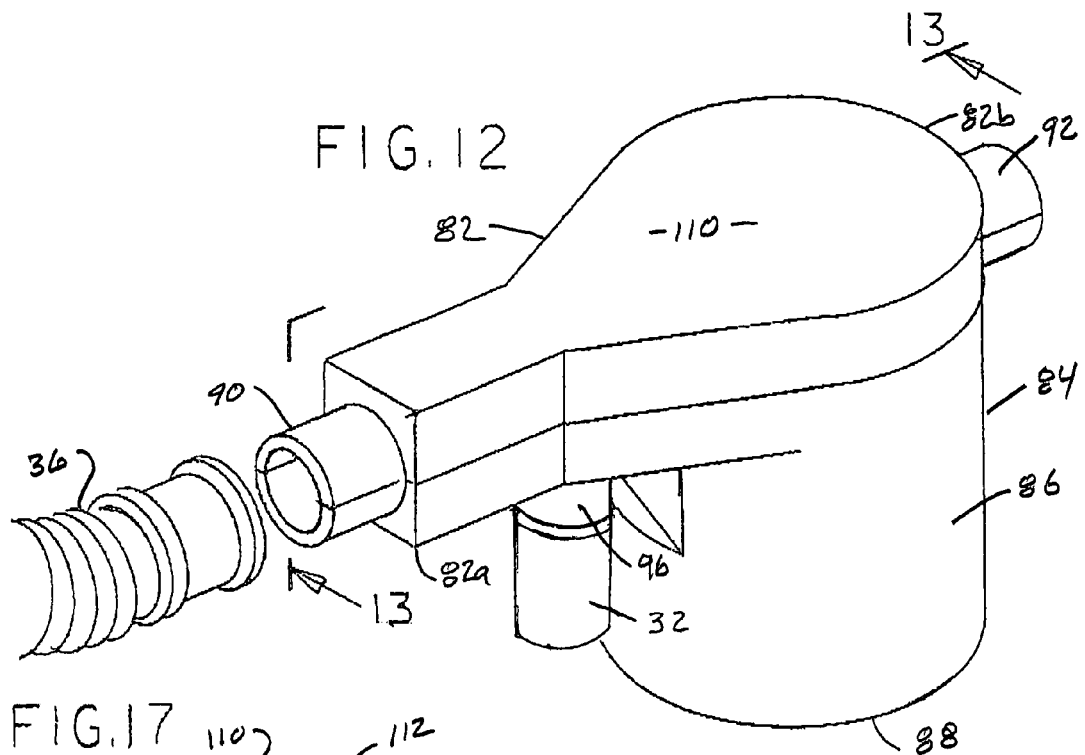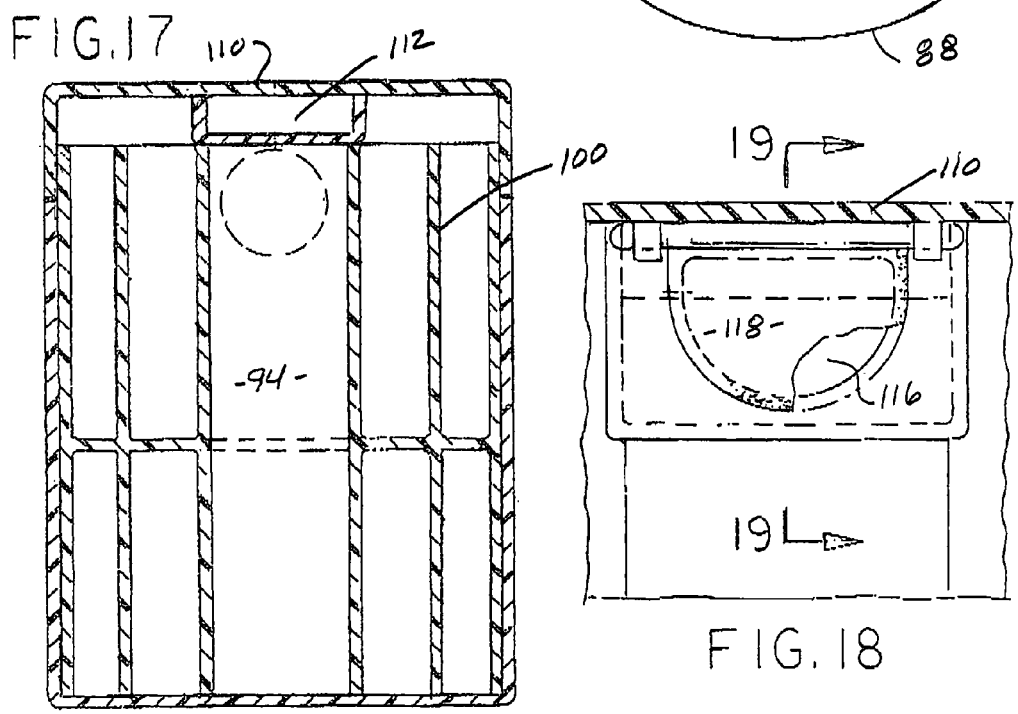

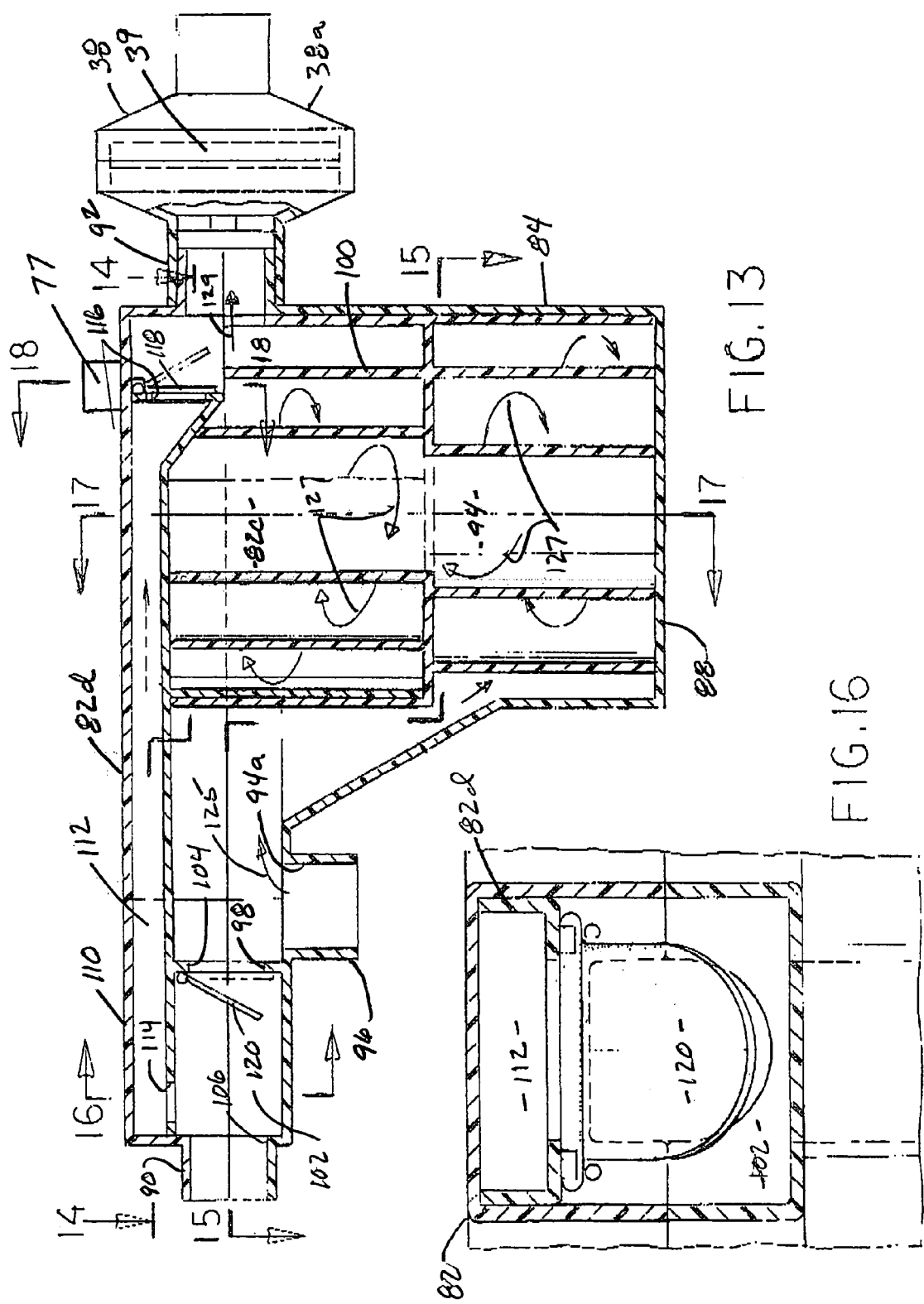

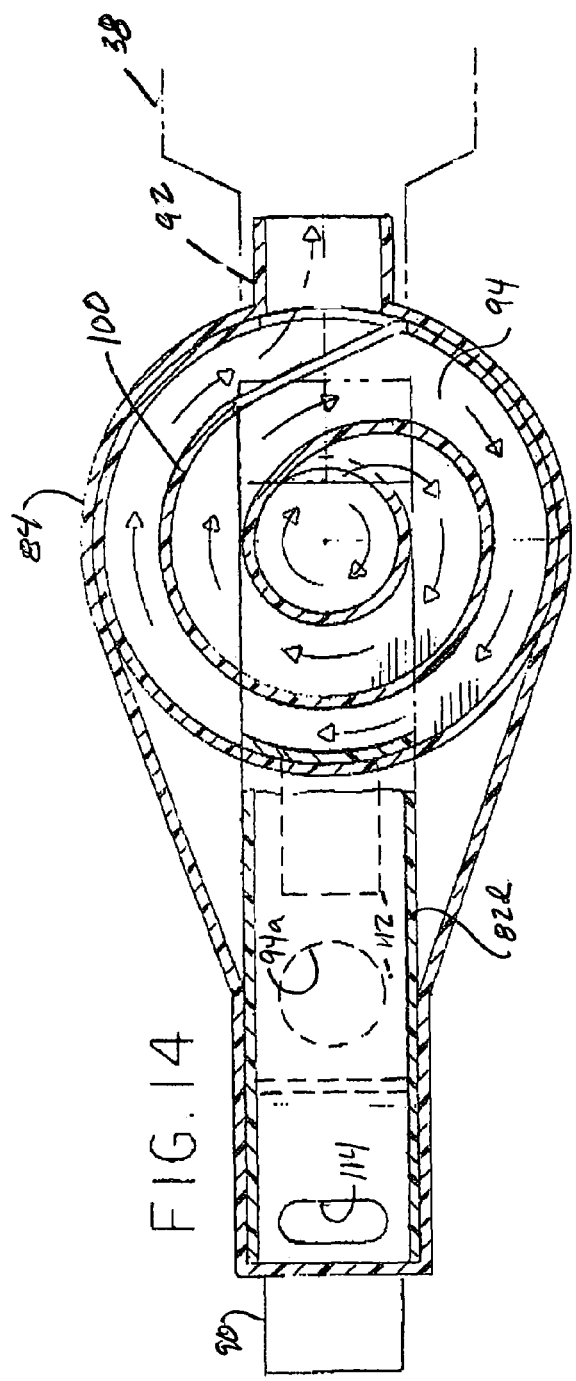
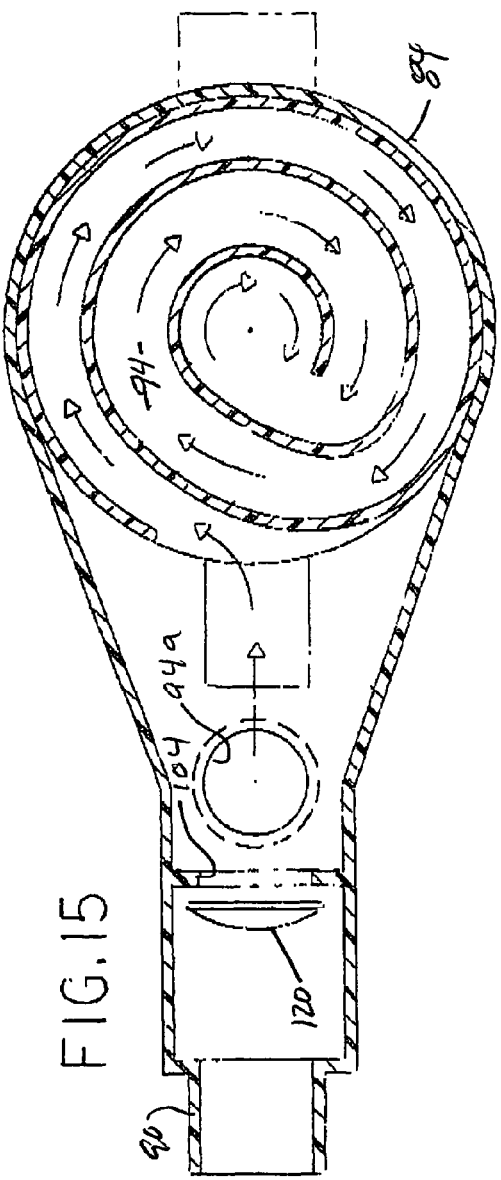
FIG.14
FIG.15

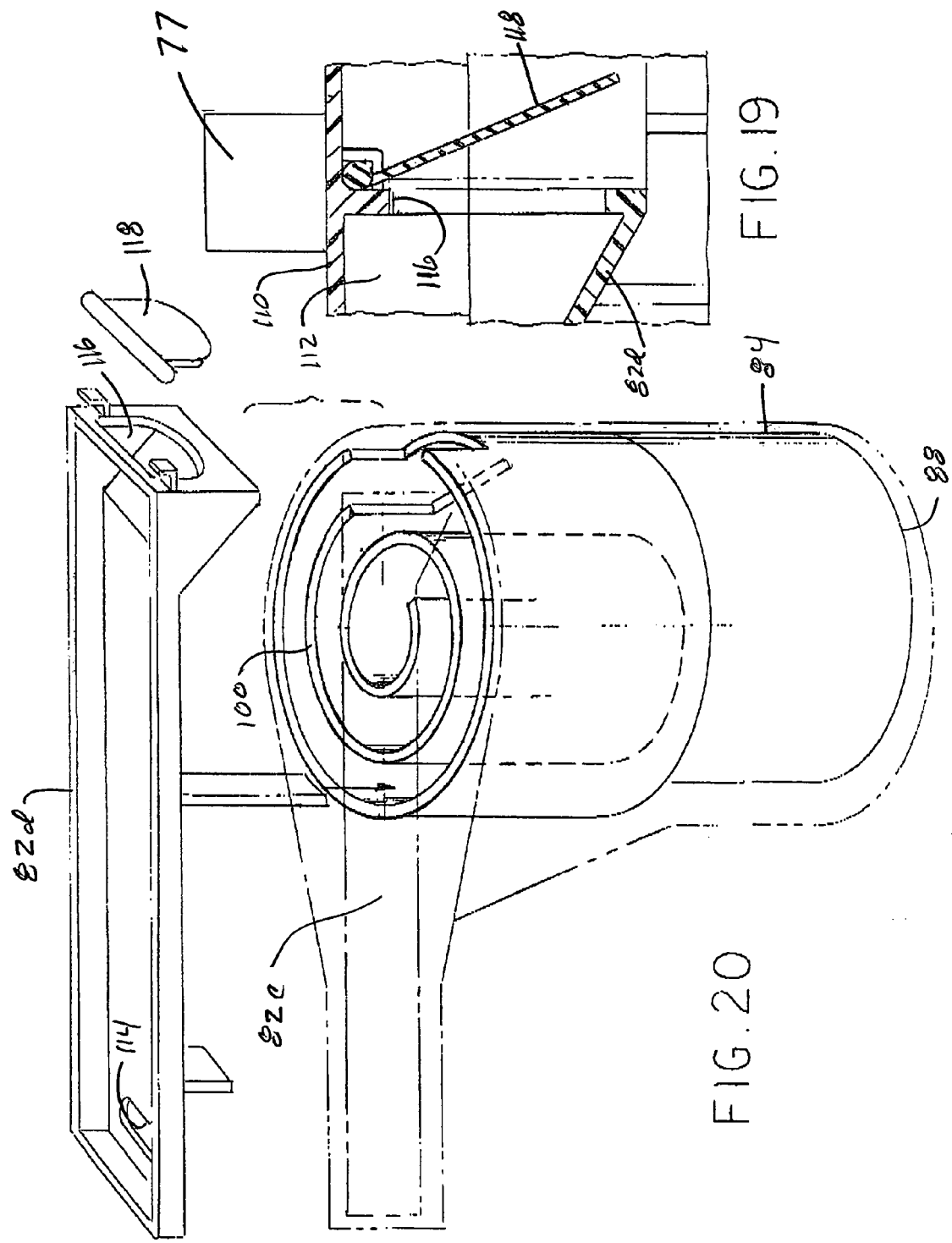

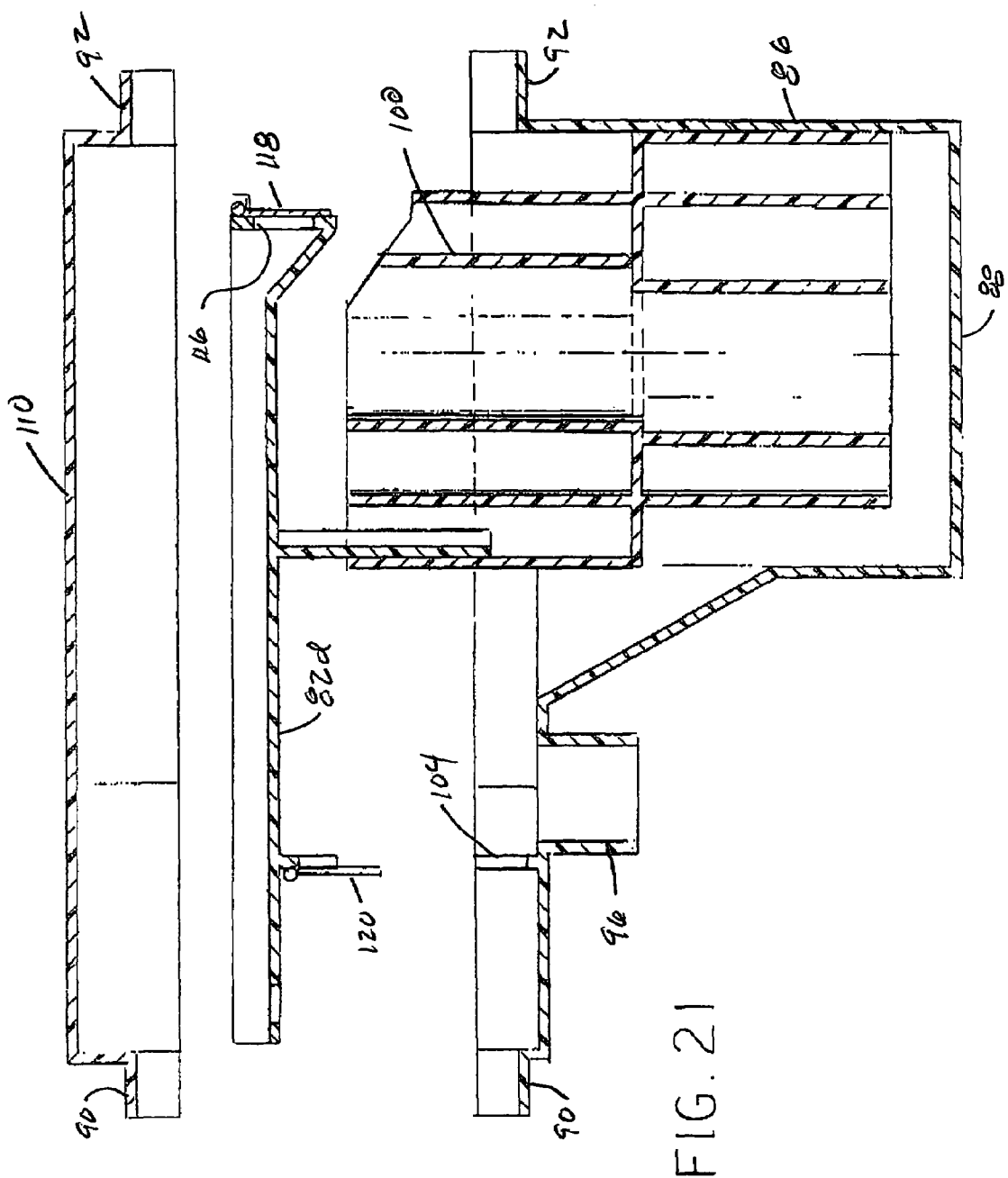

INHALATION APPARATUS

BACKGROUND OF THE INVENTION

1. Field of the Invention

The present invention relates generally to inhalation devices. More particularly, the invention concerns an improved aerosol inhalation apparatus for medicinal use that delivers a mist of properly sized aerosol particles of medicament to the patient with a very high-level of efficiency.

2. Discussion of the Prior Art

Therapeutic aerosols are commonly administered to patients suffering from numerous types of pulmonary diseases. Specific medications include beta.sub.2 agonizes, anticholinergies, cromolyn sodium, and steroids. More recently the aerosol method of delivery has been used to administer Pentamidine to patients afflicted with AIDS, Tobramycin for cystic fibrosis, Morphine for pain, and is presently under consideration as a delivery means for use in drug delivery using gene therapy. Experience has shown that the use of aerosols to treat lung disease is highly advantageous in that it produces optimal therapy with minimum side effects.

Both physical and clinical factors affect aerosol deposition in the lungs. Physical factors include inertial impaction, sedimentation, and diffusion. Clinical factors include particle size, ventilatory pattern and lung function. Aerosols larger than 5 micron mass median aerodynamic diameter (MMAD) poorly penetrate the upper respiratory tract. Those in the 1 to 2 micron range tend to have their maximum deposition in the lung parenchyma.

In general the devices used for producing medical aerosols fall into two categories; the small volume nebulizer (SVN), and the metered dose inhaler (MDI). The small volume nebulizer (SVN) has traditionally been the apparatus of choice for delivery of therapeutic aerosols. The delivery apparatus typically consists of a disposable or reusable nebulizer, a mouthpiece or facemask, and a pressurized gas source usually oxygen or air. The metered dose inhaler (MDI), on the other hand, typically contains the active drug, a metering valve, and chlorofluorcarbon (CFC) or hydrofluoroalkanes (HFA) propellants. The drug-containing canister of the device is generally fitted to a mouthpiece actuator and activation by compression of the canister into the mouthpiece results in the release of a unit dose of medication.

As stated in current literature (*Respiratory Care*, Vol. 38, No. 38, August 93, and *Advance for Respiratory Care Practitioners*, Aug. 9, 1993, pages 8-10) the most limiting factor in the use of aerosolized medication is the inefficient mist production by current commercial nebulizer systems, whether they are of the small volume nebulizer (SVN) or metered dose inhaler (MDI) variety. Research has shown that most state-of-the-art commercial units deliver less than 10% of the original dose of medication to the patient's respiratory tract. (*Respiratory Care*, Vol. 38, #8, August 1993, Page 877, and *AARC Times*, June 1993, Page 48.) The apparatus of the present invention provides a very substantial improvement over all existing prior art aerosol devices by increasing the efficiency of delivery of medication to the patient by a factor of 2 to 3 times that exhibited by currently available prior art nebulizer devices. As a further substantial benefit, the apparatus of the present invention functions in a manner to assure that the medicament particles delivered to the patient will be of optimum size for drug delivery to any or all areas of the lung where it can most effectively be utilized.

A highly successful general purpose aerosol inhalation apparatus for use in respiratory therapy procedures in the field of medicine is disclosed in U.S. Pat. No. 5,727,542 issued to the present inventor. The apparatus described in this patent converts liquid medication into an aerosol mist and provides for delivery of this mist with such high efficiency that up to 40% of the original dose of medication placed in the nebulizer can be delivered to the patient's lungs. The present invention comprises an improvement to the apparatus disclosed in U.S. Pat. No. 5,727,542 and provides for delivery of the aerosol mist to the patient at substantially equal efficiency. The present invention can also deliver drugs at these high efficiencies to patients on ventilators, where the device disclosed in U.S. Pat. No. 5,727,542 cannot.

SUMMARY OF THE INVENTION

It is an object of the present invention to provide an inhalation apparatus which will deliver an aerosolized medication to the patient, which comprises up to about 80% of the medication aerosolized.

Another object of the invention is to provide an apparatus of the aforementioned character, which will deliver to the patient essentially the same particle size distribution of the aerosol mist that originates from the nebulizer itself.

Another object of the invention is to provide delivered dose consistency even over a wide range of patient breathing parameters.

Another object of the invention is to provide a novel inhalation device, which will deliver known amounts of aerosolized medication to patients while on respirators.

Another object of the invention is to provide an apparatus, which releases only minimal amounts of drug to atmosphere.

Yet another object of the invention is to provide means for safely filtering air exhaled from the patient before its release to room atmosphere.

Still another object of the invention is to provide an inhalation apparatus of the general character described in the preceding paragraphs which can be used with a conventional ventilator.

BRIEF DESCRIPTION OF THE DRAWINGS

FIG. 2 is an enlarged, longitudinal cross-sectional view of the inhalation apparatus shown in FIG. 1.

FIG. 3 is a front view out of one of the flow control valves of the apparatus of the invention.

FIG. 4 is an enlarged cross-sectional view of the area designated as 4 in FIG. 2.

FIG. 12 is a generally perspective view of an alternate form of the inhalation apparatus of the invention.

FIG. 13 is a cross-sectional view taken along lines 13-13 of FIG. 12.

FIG. 14 is a cross-sectional view taken along lines 14-14 of FIG. 13.

FIG. 15 is a cross-sectional view taken along lines 15-15 of FIG. 13.

FIG. 16 is an enlarged cross-sectional view taken along lines 16-16 of FIG. 13.

FIG. 17 is a cross-sectional view taken along lines 17-17 of FIG. 13.

FIG. 18 is an enlarged cross-sectional view taken along lines 18-18 of FIG. 13.

FIG. 19 is a cross-sectional view taken along lines 19-19 of FIG. 18.

FIG. 20 is a generally perspective, exploded view of the apparatus of this latest form of the invention.

FIG. 21 is an exploded, longitudinal cross-sectional view of the apparatus shown in FIG. 20.

DESCRIPTION OF THE INVENTION

Figure 1:
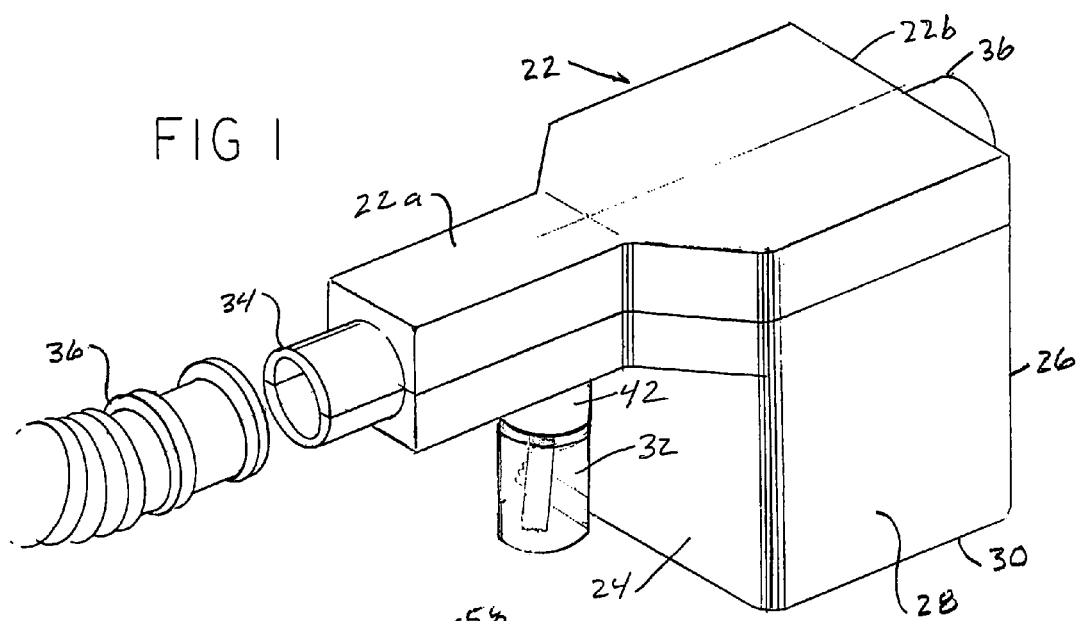
FIG. 1 is a generally perspective view of one form of the inhalation apparatus of the invention.
Figure 5:
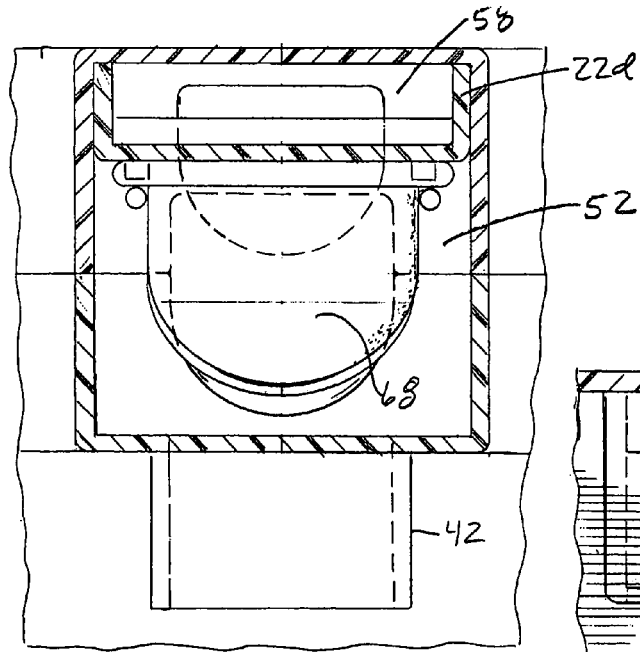
FIG. 5 is an enlarged cross-sectional view taken along lines 5-5 of FIG. 2.
Figure 6:
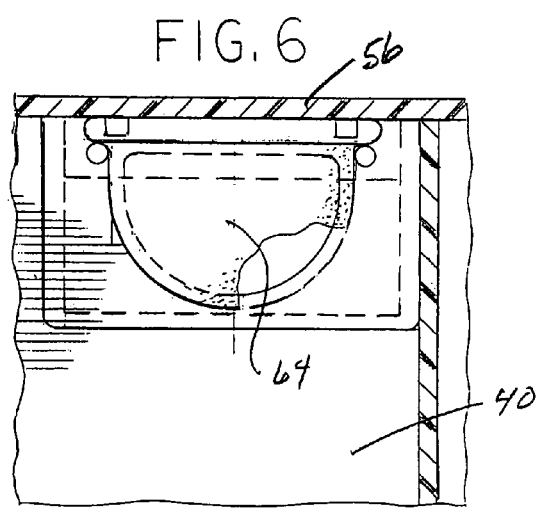
FIG. 6 is an enlarged cross-sectional view taken along lines 6-6 of FIG. 2.
Figure 7:
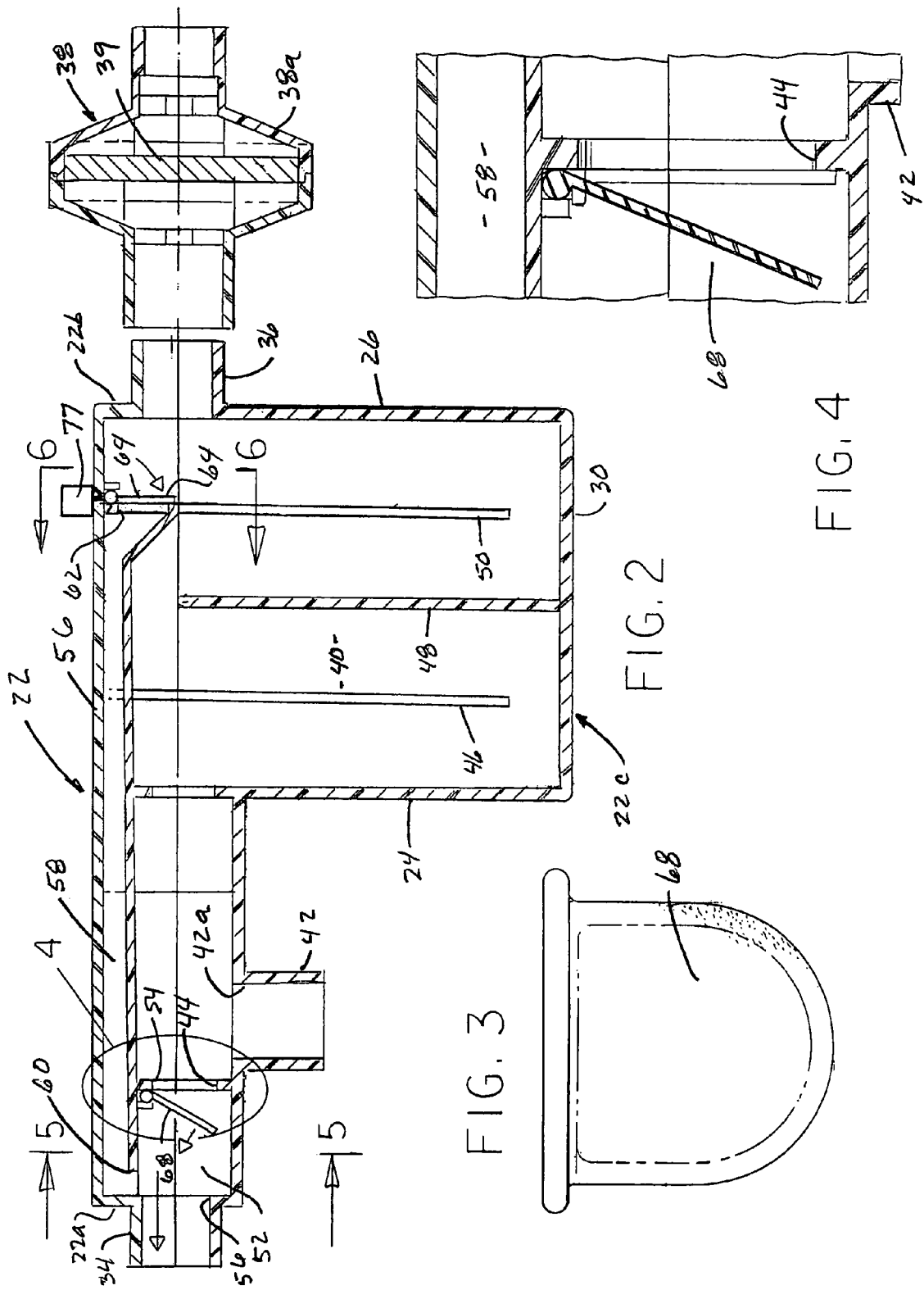
FIG. 7 is a generally perspective, exploded view of the housing of the apparatus shown in FIG. 1 illustrating internal construction.

Referring to the drawings and particularly to FIGS. 1 and 2, the aerosol inhalation apparatus of one form of the invention is there shown and can be seen to comprise a housing 22 which includes interconnected front, back, side and bottom walls 24, 26, 28 and 30 respectively. Attached to housing 22 is a nebulizer means, shown here as a conventional, small volume nebulizer (SVN) 32 (FIG. 1). A first end 22a of the main housing is provided with a standard size breathing port 34 for ready patient interfacing with the aerosol system. A second end 22b of the main housing is provided with an outlet port 36 to which filter means, shown here as a filter assembly 38 can be interconnected (FIG. 2) if so desired.

Figure 8:
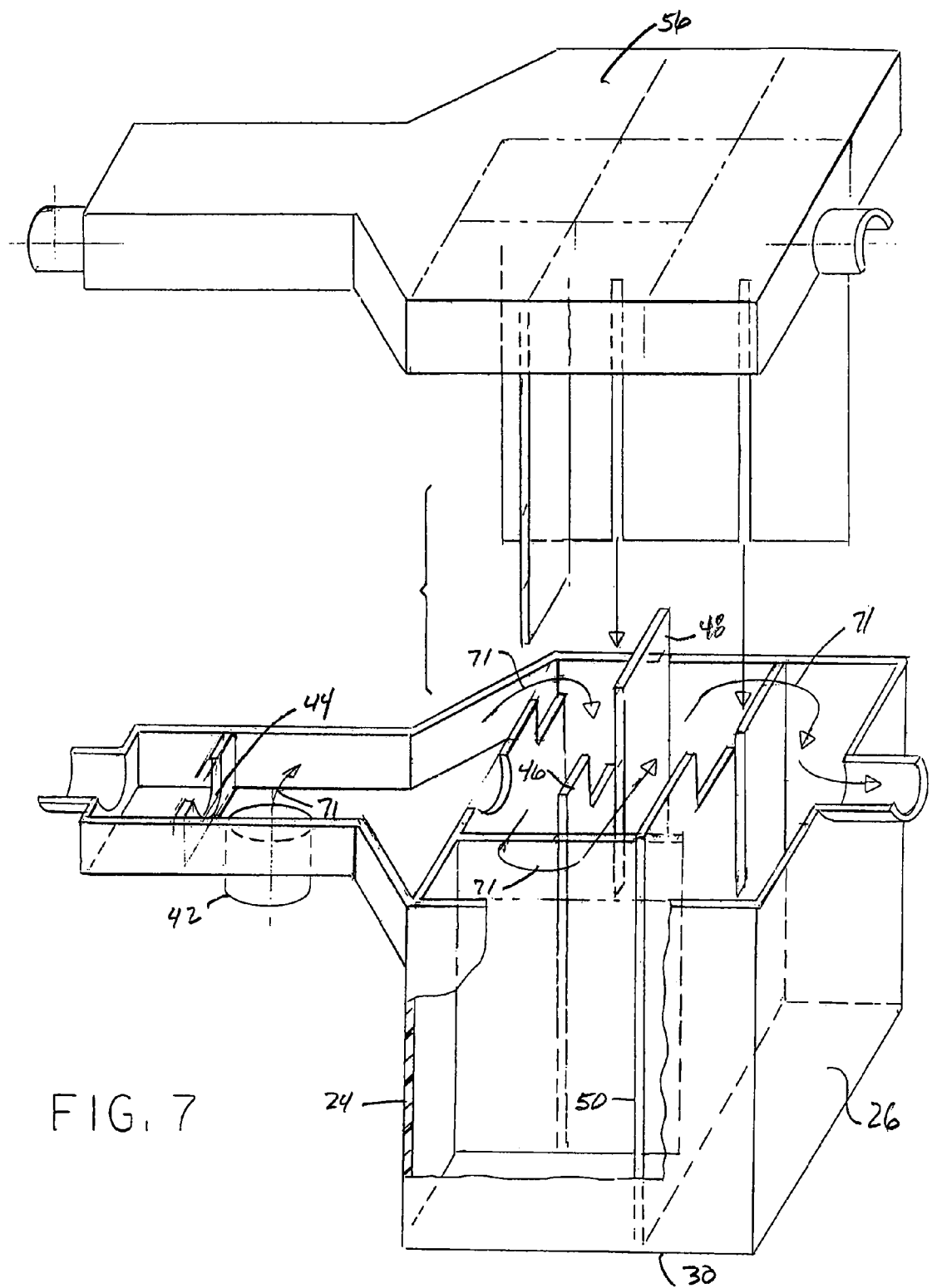
FIG. 8 is a generally perspective view of a chamber defining insert receivable within the housing portion of the apparatus of the invention.
Figure 9:
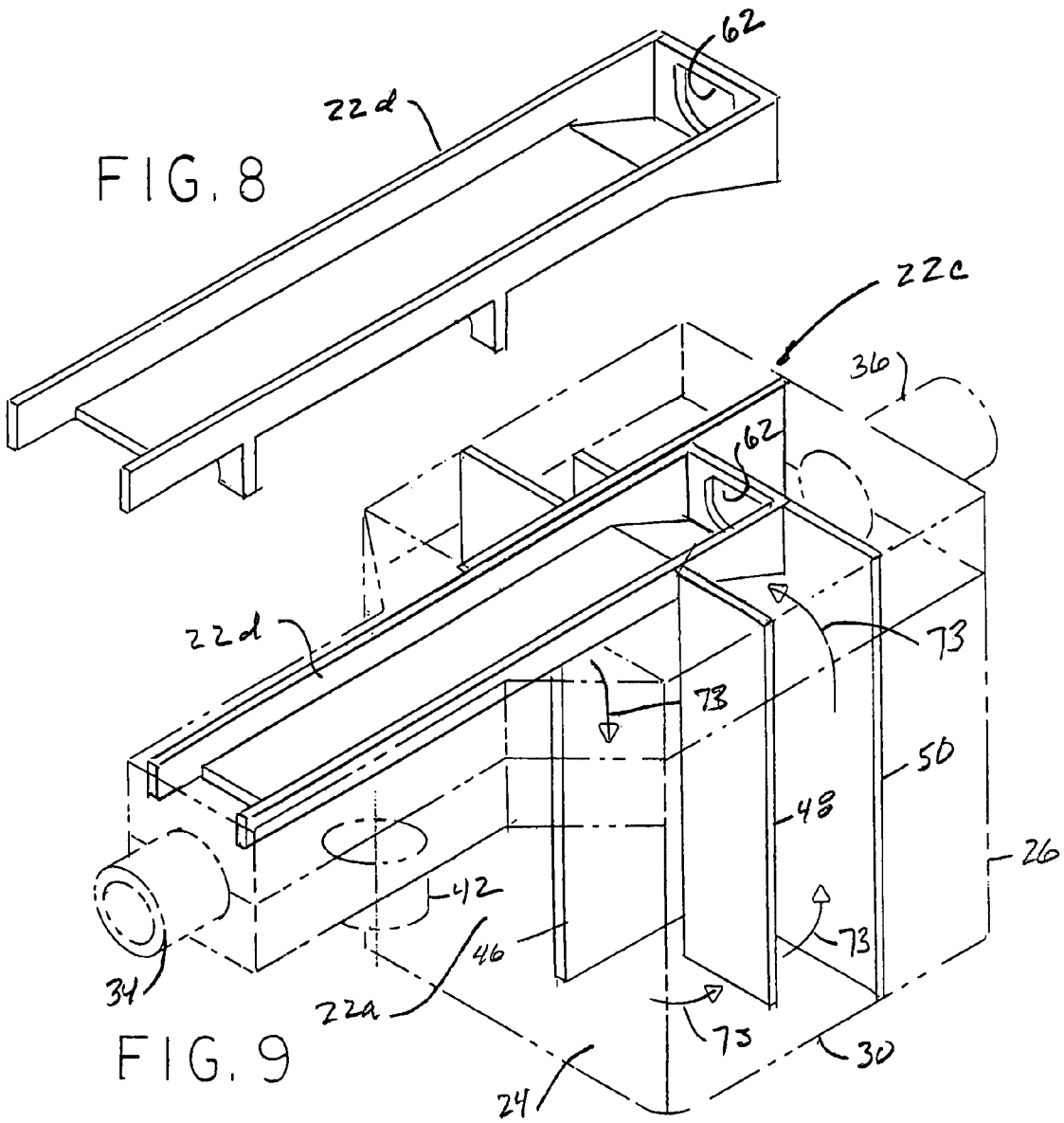
FIG. 9 is a generally perspective view illustrating of the manner of positioning the chamber defining insert shown in FIG. 8 within the main housing portion of the apparatus.

As best seen by referring to FIGS. 2, 8 and 9, housing 22 includes a main portion 22c and a chamber defining, insert portion 22d which is received within main portion 22c in the manner shown by the solid lines in FIG. 9. Housing 22 also includes a first chamber 40 having an inlet 42a defined by an inlet port 42, an outlet 44 and baffle means for providing a circuitous fluid flow path through the first chamber. In the present form of the invention this important baffle means comprises a plurality of longitudinally spaced-apart, strategically configured baffles or walls 46, 48 and 50. Housing 22 also includes a second chamber 52 having an inlet 54 in communication with a first chamber 40 and an outlet 56 in communication breathing port 34. Insert portion 22d in cooperation with a housing top wall 56 defines a third chamber 58 chamber having an inlet 60 in communication with said second chamber 52 and an outlet 62, which communicates with outlet port 36 via a first flow control means, here provided as a flapper valve mechanism 64.

As shown in FIG. 1, nebulizer 32 is interconnected with inlet port 42 for communication with first chamber 40 for nebulizing a fluid medication containing the medicament to produce a particulate laden spray and for introducing said particulate laden spray into first chamber 40.

A second flow control means, shown here as valve member 68 is pivotally movable relative to inlet 54 of said second chamber 52 for controlling fluid flow through the inlet and into second chamber 52.

Before discussing the operation of the apparatus of the invention as described in the preceding paragraphs, a brief discussion of the theory of patient inhalation and dose quantification is believed appropriate. In this regard, the breathing cycle for a patient involves an inhalation and exhalation component, usually in a time ratio of one part inhalation and two parts exhalation (i.e. 1:2). As an example, if a patient is breathing at a rate of 12 breaths per minute (BPM) the complete breathing cycle would involve 5 seconds (60 sec./12 BPM=5 sec.), and at a 1:2 inhalation/exhalation ratio, the exhalation time would be in the order of 3.3 seconds. When a normal nebulizer configuration is used, the drug as aerosolized by the nebulizer is blown into the atmosphere for ⅔s of each breathing cycle. If this aerosol could be retained and added to that received during the next patient inhalation, system efficiency would be greatly enhanced and the delivered patient dose should be quantifiable. The reservoir component of the present invention, when used with an air/oxygen flow rate of 7-8 liters per minute (LPM) to the nebulizer, is the correct volume to allow for this needed medication retention. Determination of the minimum volume needed is as follows:

$$\frac{60 \text{ sec.}}{12 \text{ BPM}} (5 \text{ seconds})(2/3) = 3.3 \text{ second exhalation}$$

$$\frac{(3.3 \text{ seconds})(7,000 \text{ ml/min.})}{60} = 385 \text{ ml. volume}$$

Knowing that medication lost is very small, and in general a relatively fixed percentage of that aerosolized, quantification of the patient dose received is very possible using the following equation:

Inhaled Dose=(drug concentration)(drug mass aerosol rate [DMAR])(system efficiency)(time).

Where drug concentration is known at the start of the procedure; DMAR is an easily determined fixed number for a given nebulizer at a defined oxygen flow rate; system efficiency is a relatively fixed number for given system; and time is the system run time determined prior to start, or just prior to nebulizer sputter.

With the foregoing in mind, it can be seen that reservoir chamber 40 consists of a fixed, determinable volume. As indicated by the previous calculations, in practice, chamber 40 preferably has a minimum volume of about 400 ml., which approximately equals the volume of aerosol produced by the nebulizer 32 during the time of patient exhalation under typical conditions such as an oxygen flow rate of about 7 liters per minute, a breathing rate of approximately 12 breaths per minute and an "in-out" ratio of about 1:2.

Figure 10:
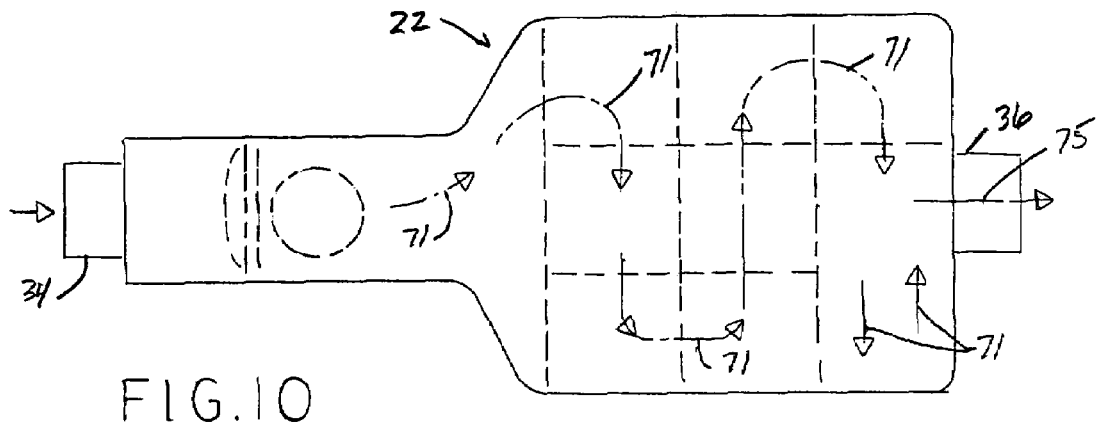
FIG. 10 is a generally diagrammatic, top plan view of the apparatus illustrating the fluid flow path through the various cooperating chambers of the apparatus.
Figure 11:
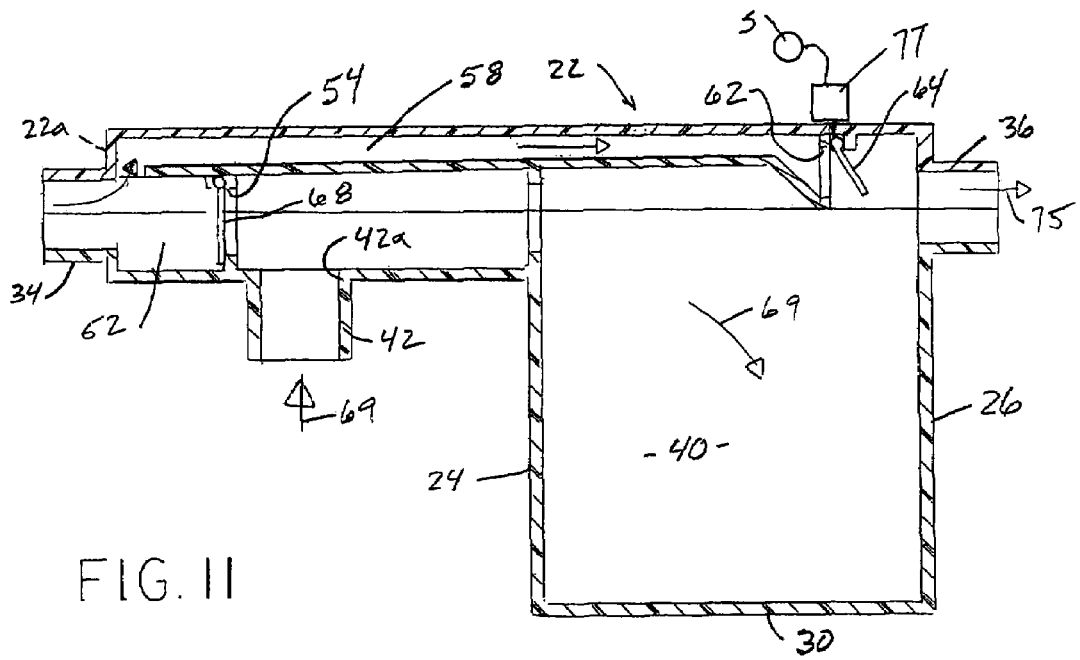
FIG. 11 is a generally diagrammatic, cross-sectional view of the apparatus further illustrating the fluid flow path through the various cooperating chambers of the apparatus.

Referring to FIG. 11, it can be seen that upon patient exhalation, the. expired air will pass through chamber 22 and first control means flapper valve number 64, and exiting the device through port 75. In so doing air pressure against second flow control means, here shown as a conventional, flapper-type valve member 68, which is pivotally movable relative to inlet 54 of second chamber 52, moves from the open position shown in FIG. 2 into the closed position shown in FIG. 11. With a valve member 68 closed, the aerosol, which is being newly generated by the nebulizer 32, flows into chamber 40 in the manner indicated by the arrows 69. As indicated by the arrow 71 in FIG. 10, as the newly generated aerosol flows into chamber 40, the residual air contained within the chamber will flow around and about the interior baffles 46, 48 and 50 in the manner indicated by the arrows 73 in FIG. 9 and will be pushed outwardly through exhaust port 36 in the manner indicated by the arrow 75 of FIG. 11.

As previously discussed, duration of the expiration will be in the order of 3-4 seconds or less during which the newly generated aerosol will fill all pathways in chamber 40. Next, upon patient inhalation, atmospheric air will be drawn in through port 36 causing valve member 64 to close and through displacement force all aerosol in reservoir 40 to pass through flow control means 54 and out to the patient. Additionally, during this time of patient inhalation, aerosol coming from continuously operating nebulizer member 32 (FIG. 1) is also being received by the patient. It can be readily seen by those skilled in the art that drug is delivered very efficiently, and drug loss is not only minimal but essentially a constant percentage of that aerosolized.

In summary, due to the unique design of the apparatus of the invention, essentially all of the aerosolized medication (only loss—a relatively small percentage retained in the body of the device) is accessed by the patient and the effects of patient breathing parameters are minimized or eliminated. Knowing the initial drug concentration (mg./ml) and the patient breathing time on the system, the inhaled dose can be easily calculated, generally within ±12%. Conversely, if the desired inhaled dose is known, the same equation can be revised as follows to determine patient-breathing time required:

$$\text{Breathing Time} = \frac{\text{Desired Patient Dose}}{(\text{drug concentration})(DMAR)(\text{system efficiency})}$$

Figure 11A:
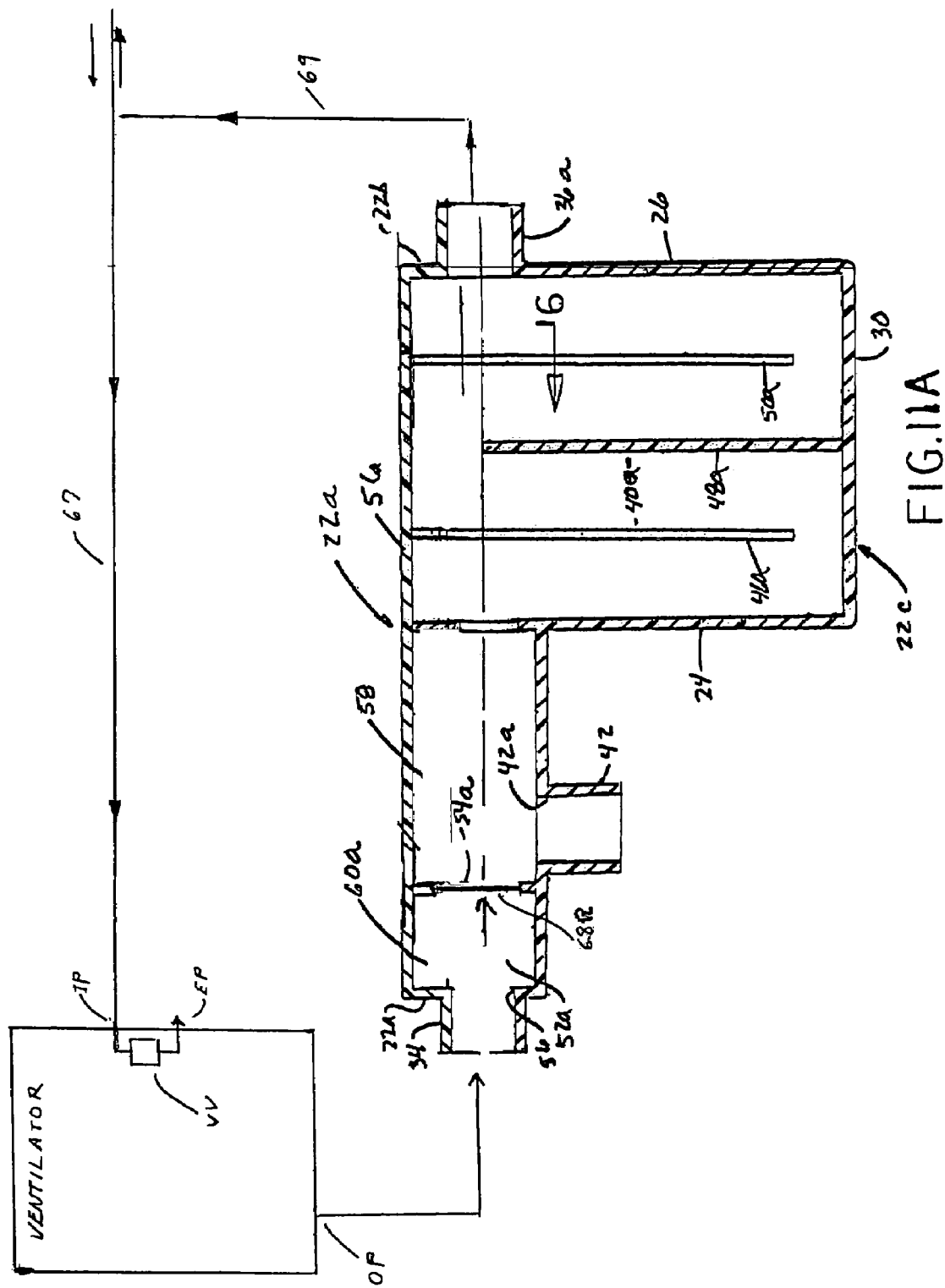
FIG. 11A is a generally diagrammatic, cross-sectional view of an alternate form of the invention that can be used with a conventional ventilator apparatus.

Referring now to FIG. 11A, an alternate form of the apparatus of the invention, which can be used with a conventional ventilator, is there shown. This apparatus is similar in many respects to that shown in FIGS. 1 through 11 and like numerals are used in FIG. 11A to identify like components. As will be presently described, with proper placement in the breathing circuit this device can deliver drugs with essentially the same efficiencies as that previously described when used in conjunction with patients when connected to ventilators. In this latest embodiment of the invention, insert portion 22d with flapper valve 64 is omitted, and replaced with a valve means for controlling fluid flow between the outlet port OP of the ventilator through an inlet chamber 52a and into a baffle chamber 40a of housing 22a. Baffle chamber 40a is provided with spaced-apart baffles, 46a, 48a and 50a. Valve means 68R, which is the reverse of valve 68, functions to open and close a port 54a as needed for injection of pressurized air from the ventilator. This actuation of air pressure forces medicated air/oxygen from chamber 60a and chamber 40a through exit port 36a to the patient. Automatic operation of the ventilator circuitry is such that at such time air pressure from port OP of the ventilator is applied at port 34 an internal valve VV in the ventilator tightly closes the air exit tube from the patient, creating a completely closed circuit. Upon completion of the "inhalation" procedure, valve 68R moves into its closed position, the ventilator valve VV of the ventilator opens and the expired air from the patient flows in the direction of the arrows through conduit 67 which is in communication with the patient. Upon closure of valve 68R, newly generated aerosol once again fills chamber 40a thereby completing the cycle.

Turning next to FIGS. 12 through 21 an alternate form of the aerosol inhalation apparatus of the invention is there shown and generally designated by the numeral 80. This alternate form of the apparatus of the invention is similar in some respects to that shown in FIGS. 1 through 11 and like numerals are used in FIGS. 12 through 21 to identify like, components. As best seen by referring to FIGS. 12 and 13, this latest form of the apparatus can be seen to comprise a housing 82 which includes a generally cylindrically-shaped main body portion 84 having interconnected side and bottom walls 86 and 88 respectively. Attached to housing 82 is a nebulizer means, shown here as the previously identified, small volume nebulizer (SVN) 32 (FIG. 12). A first end 82a of the main housing is provided with a standard size breathing port 90 for ready patient interfacing with the aerosol system. A second end 82b of the main housing is provided with an outlet port 92 to which filter means, such as the previously identified filter assembly 38 can be interconnected (FIG. 13).

As best seen by referring to FIGS. 13 and 20, housing 82 includes a main portion 82c and a chamber defining, insert portion 82d which is received within main portion 82c in the manner shown in the drawings. The generally cylindrically-shaped portion 84 of housing 82 includes a first chamber 94 having an inlet 94a defined by an inlet port 96, an outlet 98 and baffle means for providing a circuitous fluid flow path through the first chamber. In this latest form of the invention this important baffle means comprises a generally spiral-shaped wall 100 (FIG. 20). Housing 82 also includes a second chamber 102 having an inlet 104 in communication with a first chamber 94 and an outlet 106 in communication breathing port 90.

Insert portion 82d in cooperation with a housing top wall 110 defines a third chamber 112 chamber having an inlet 114 in communication with said second chamber 102 and an outlet 116, which communicates with outlet port 92 via a first flow control means, here provided as a flapper valve mechanism 118.

As shown in FIG. 12, nebulizer 32 is interconnected with inlet port 96 for communication with first chamber 94 for nebulizing a fluid medication containing the medicament to produce a particulate laden spray and for introducing said particulate laden spray into first chamber 94.

A second flow control means, shown here as valve member 120, is pivotally movable relative to inlet 98 of chamber 102 for controlling fluid flow through the inlet and into chamber 102.

With the previous discussion of the theory of patient inhalation and dose quantification in mind, it can be seen that reservoir chamber 94 consists of a fixed, determinable volume. In practice, chamber 94 preferably has a volume of about 400 ml., which approximately equals the volume of aerosol produced by the nebulizer 32 during the time of patient exhalation under typical conditions such as an oxygen flow rate of about 7 liters per minute, a breathing rate of approximately 12 breaths per minute and an "in-out" ratio of about 1:2.

In using this latest form of the apparatus of the invention, upon patient exhalation, the second flow control means, here shown as a conventional, flapper-type valve member 120, which is pivotally movable relative to inlet 104 of second chamber 102, moves from the open position shown by the solid lines in FIG. 13 into the closed position shown by the dotted lines in FIG. 13. With a valve member 120 closed, the aerosol, which has been newly generated by the nebulizer 32 flows into chamber 94 in the manner indicated by the arrows 125. As the newly generated aerosol flows into chamber 94, the residual air contained within the chamber will flow through the use or this flow path defined by spiral wall 100 in the manner indicated by the arrows 127 in FIG. 13 (see also the arrows in FIGS. 14 and 15) and will be pushed outwardly through exhaust port 92 in the manner indicated by the arrow 129 of FIG. 13.

In response to patient exhalation, valve member 118 is opened in the manner shown by the dotted lines in FIG. 13. At the same time, exhalation by the patient closes valve 120. Simultaneously the nebulizer 32 is producing medicated aerosol, which replenishes the reservoir chamber, or chamber 94.

In summary, due to the unique design of this alternate form of the apparatus of the invention, essentially all of the aerosolized medication (only loss—a relatively small percentage retained in the body of the device) is accessed by the, patient and the effects of patient breathing parameters are minimized or eliminated. Knowing the initial drug concentration (mg./ml) and the patient breathing time on the system, the inhaled dose can be easily calculated, generally within ±12%. Conversely, as discussed in connection with a first embodiment of the invention, if the desired inhaled dose is known, the same equation can be revised to determine patient breathing time required.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An aerosol inhalation apparatus for delivering a medicament containing mist to a patient comprising:
   (a) a housing including:
      (i) a first chamber having an inlet, an outlet and baffle means for providing a circuitous fluid flow path through said first chamber; and
      (ii) a second chamber having an inlet in communication with said first chamber and an outlet; and
      (iii) a third chamber having an inlet in communication with said second chamber, and an outlet in communication with said first chamber; and
   (b) nebulizing means connected to said housing for communication with said first chamber for nebulizing a fluid medication containing the medicament to produce a particulate laden spray and for introducing said particulate laden spray into said first chamber;
   (c) a first flow control means for controlling fluid flow outwardly of said outlet of said third chamber; and
   (d) a second flow control means for controlling fluid flow between said outlet of said first chamber and said second chamber.

2. The aerosol inhalation apparatus as defined in claim 1, in which said first flow control means comprises a valve member pivotally movable relative to said outlet of said third chamber for controlling fluid flow through said outlet of said third chamber.

3. The aerosol inhalation apparatus as defined in claim 1, in which said second flow control means comprises a valve member pivotally movable relative to said inlet of said second chamber for controlling fluid flow through said inlet.

4. The aerosol inhalation apparatus as defined in claim 1 in which said baffle means comprises a plurality of spaced-apart baffles disposed within said first chamber.

5. The aerosol inhalation apparatus as defined in claim 1 in which said baffle means comprises a generally spiral-shaped wall defining a circuitous flow path.

6. The aerosol inhalation apparatus as defined in claim 1 in which said housing comprises a main portion and an insert portion interconnected with said main portion, said insert portion defining a chamber.

7. The aerosol inhalation apparatus as defined in claim 1, further including filter means interconnected with said outlet of said first chamber.

8. The aerosol inhalation apparatus as defined in claim 1, further including a breathing tube interconnected with said outlet of said second chamber.

9. The aerosol inhalation apparatus as defined in claim 1 in which said housing comprises a generally cylindrically-shaped portion and a chamber defining, insert portion interconnected with said generally cylindrically-shaped portion.

10. An aerosol inhalation apparatus for delivering a medicament containing mist to a patient comprising:
    (a) a housing including:
       (i) a first chamber having an inlet, an outlet and baffle means for providing a circuitous fluid flow path through said first chamber;
       (ii) a second chamber having an inlet in communication with said first chamber and an outlet;
       (iii) a third chamber having an inlet in communication with said second chamber and an outlet in communication with said first chamber;
    (b) nebulizing means connected to said housing for communication with said first chamber for nebulizing a fluid medication containing the medicament to produce a particulate laden spray and for introducing said particulate laden spray into said first chamber;
    (c) a first flow control means for controlling fluid flow between said outlet of said third chamber and said first chamber, said first flow control means comprises a pivotally mounted valve member for controlling fluid flow through said outlet of said third chamber; and
    (d) a second flow control means for controlling fluid flow between said outlet of said first chamber and said inlet of said second chamber, said second flow control means comprising a flapper valve pivotally mounted proximate said inlet of said second chamber for controlling fluid flow through said inlet.

11. The aerosol inhalation apparatus as defined in claim 10 in which said second flow control means is operated by patient exhalation.

12. The aerosol inhalation apparatus as defined in claim 10, in which said first flow control means comprises a valve member pivotally movable relative to said outlet of said third member for controlling fluid flow through said outlet of said third chamber.

13. The aerosol inhalation apparatus as defined in claim 10 in which said baffle means comprises a plurality of spaced-apart baffles disposed within said first chamber.

14. The aerosol inhalation apparatus as defined in claim 10 in which said baffle means comprises a generally spiral-shaped wall defining a circuitous flow path.

15. The aerosol inhalation apparatus as defined in claim 10 in which said housing comprises a main portion and a chamber defining, insert portion interconnected with said main portion.

16. The aerosol inhalation apparatus as defined in claim 10, further including filter means interconnected with said outlet of said first chamber.

17. The aerosol inhalation apparatus as defined in claim 10, further including a breathing tube interconnected with said outlet of said second chamber.

18. The aerosol inhalation apparatus as defined in claim 10 in which said housing comprises a generally cylindrically-shaped portion and a chamber defining, insert portion interconnected with said generally cylindrically-shaped portion.

* * * * *